United States Patent
Jackson et al.

(10) Patent No.: US 10,912,658 B2
(45) Date of Patent: Feb. 9, 2021

(54) ARTHROPLASTY APPARATUS AND METHOD

(71) Applicant: Oxford University Innovation Limited, Oxford (GB)

(72) Inventors: William Jackson, Oxford (GB); Andrew Price, Oxford (GB)

(73) Assignee: OXFORD UNIVERSITY INNOVATION LIMITED

( * ) Notice: Subject to any disclaimer, the term of this patent is extended or adjusted under 35 U.S.C. 154(b) by 241 days.

(21) Appl. No.: 15/566,383

(22) PCT Filed: Apr. 14, 2016

(86) PCT No.: PCT/GB2016/051040
§ 371 (c)(1),
(2) Date: Oct. 13, 2017

(87) PCT Pub. No.: WO2016/170306
PCT Pub. Date: Oct. 27, 2016

(65) Prior Publication Data
US 2018/0140440 A1    May 24, 2018

(30) Foreign Application Priority Data
Apr. 20, 2015 (GB) .................................. 1506675.6

(51) Int. Cl.
*A61F 2/46* (2006.01)
*A61B 17/15* (2006.01)
(Continued)

(52) U.S. Cl.
CPC .......... *A61F 2/4684* (2013.01); *A61B 17/157* (2013.01); *A61B 17/154* (2013.01);
(Continued)

(58) Field of Classification Search
CPC . A61B 17/155; A61B 17/157; A61B 17/1675; A61B 17/1764; A61B 17/154;
(Continued)

(56) References Cited

U.S. PATENT DOCUMENTS

| | | | | |
|---|---|---|---|---|
| 4,721,104 A | * | 1/1988 | Kaufman | A61B 17/1764 606/88 |
| 2009/0222014 A1 | * | 9/2009 | Bojarski | A61B 17/155 606/88 |
| 2010/0305575 A1 | * | 12/2010 | Wilkinson | A61B 17/155 606/88 |

FOREIGN PATENT DOCUMENTS

| | | |
|---|---|---|
| FR | 2742037 A1 | 6/1997 |
| FR | 2810227 A1 | 12/2001 |
| WO | 20110131983 A2 | 10/2011 |

OTHER PUBLICATIONS

International Search Report for Application No. PCT/GB2016/051040.

(Continued)

*Primary Examiner* — Marcela I. Shirsat
(74) *Attorney, Agent, or Firm* — Thomas|Horstemeyer, LLP

(57) ABSTRACT

A femoral trial component (16) for attachment to a prepared distal surface of a femur, the femoral trial component comprising a first fastening point (20) for coupling the femoral trial component to a tibial cutting jig. The femoral trial component may further comprise a second fastening point (21) for coupling the trial component to a tibial cutting jig (25), the first and second fastening points being at a predetermined angle (e.g. substantially 90 degrees) to one another. Advantageously the trial component may also have a cut-out region (17) for accommodating an anterior cruciate ligament.

15 Claims, 12 Drawing Sheets

(51) Int. Cl.
*A61F 2/38* (2006.01)
*A61B 17/16* (2006.01)
*A61B 17/17* (2006.01)

(52) U.S. Cl.
CPC ....... *A61B 17/1675* (2013.01); *A61B 17/1764* (2013.01); *A61B 17/1767* (2013.01); *A61F 2/389* (2013.01); *A61F 2/3859* (2013.01)

(58) Field of Classification Search
CPC .. A61B 17/1767; A61F 2/4684; A61F 2/3859; A61F 2/389
USPC .......................................................... 606/87
See application file for complete search history.

(56) References Cited

OTHER PUBLICATIONS

Written Opinion for International Application No. PCT/GB2016/051040.

\* cited by examiner

Figure 3a
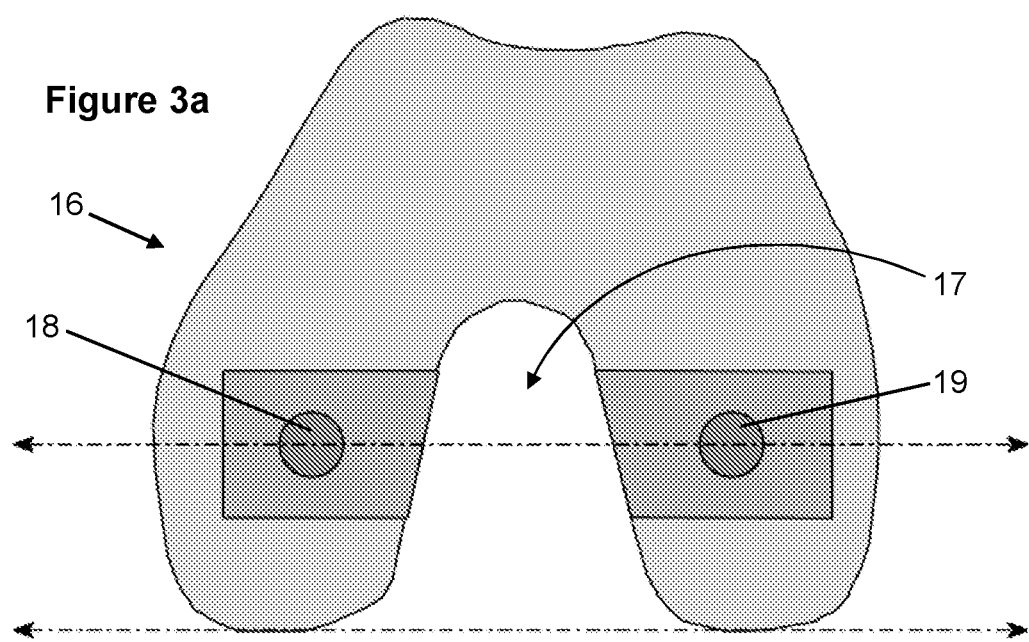
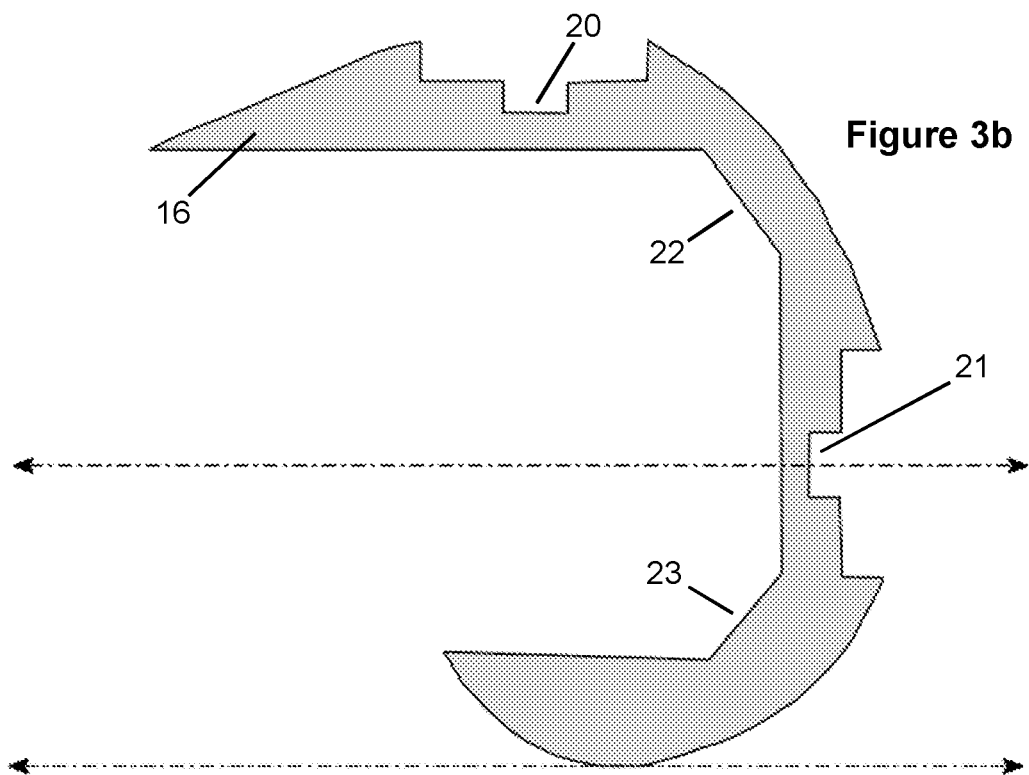
Figure 3b
Figure 3

ARTHROPLASTY APPARATUS AND METHOD

CROSS-REFERENCE TO RELATED APPLICATION

This application is the National Stage of International Application No. PCT/GB2016/051040, filed 14 Apr. 2016, which claims the benefit of and priority to GB Application No. 1506675.6, having the title "Arthroplasty Apparatus And Method," filed on 20 Apr. 2015, the entire disclosures of which are incorporated by reference in their entireties as if fully set forth herein.

FIELD OF THE INVENTION

The present invention relates to apparatus for use in carrying out an arthroplasty procedure, and a method for performing an arthroplasty procedure.

BACKGROUND TO THE INVENTION

Arthroplasty is an orthopedic surgical procedure where the articular surface of a musculoskeletal joint is replaced. It is an elective procedure that is performed in order to relieve pain and restore function to the joint after damage by arthritis, for example, or some other type of trauma.

The present work is particularly (but not exclusively) concerned with arthroplasty of the human knee. Knee arthroplasty, or knee replacement, is a surgical procedure to replace the weight-bearing surfaces of the knee joint to relieve pain and disability. It is most commonly performed for osteoarthritis, and also for other knee diseases such as rheumatoid arthritis and psoriatic arthritis.

Knee arthroplasty can be performed as partial or total knee arthroplasty. In general, the surgery consists of replacing the diseased or damaged joint surfaces of the knee with metal and plastic components shaped to allow continued motion of the knee. In partial knee arthroplasty a specific part of a joint surface of the knee is replaced, whereas in total knee arthroplasty (TKA) both the opposing surfaces of the knee joint are replaced. The present work is applicable to both these types of knee arthroplasty procedures.

To improve upon existing knee arthroplasty procedures, there is a desire to create an anatomic femoral resurfacing with a corresponding tibial resurfacing sympathetic to the soft tissue envelope, with an aim to restore normal joint line height, joint line obliquity and tibial slope. This will allow the soft tissue envelope to behave as near to normal as can be achieved given the geometry and material constraints of conventional prosthesis designs.

SUMMARY OF THE INVENTION

According to a first aspect of the invention there is provided a femoral trial component for attachment to a prepared distal surface of a femur, the femoral trial component comprising a fastening point for coupling (in a substantially rigid yet temporary manner) the femoral trial component to a tibial cutting jig. This advantageously enables a subsequent tibial resurfacing cut to be made with reference to the femoral trial component, and is applicable to both partial and total knee arthroplasty procedures.

According to an embodiment, the said fastening point is a first fastening point, and the femoral trial component further comprises a second fastening point for coupling the femoral trial component to a tibial cutting jig, the first and second fastening points being at a predetermined angle (e.g. substantially 90 degrees) to one another. This allows the position of the tibial cutting jig to be checked at different angles of flexion of the knee (for example, with the knee at full extension and at an angle of substantially 90 degrees), in both instances with reference to the femoral trial component, before the tibial cutting jig is used to resurface the tibia. In other embodiments, one or more additional fastening points, at other predetermined angles, may also be provided on the femoral trial component, in addition to the first and second fastening points.

Advantageously the femoral trial component may also have a cut-out region for accommodating an anterior cruciate ligament.

The femoral trial component may be provided in a set of parts together with a tibial cutting jig, and coupling means for reversibly coupling the tibial cutting jig to the femoral trial component via the first fastening point.

If the femoral trial component is provided with a second fastening point, or additional fastening point(s), then the coupling means provided in the set of parts are for reversibly coupling the tibial cutting jig to the femoral trial component via the first fastening point and, separately, via the second (or additional) fastening point(s).

According to a second aspect of the invention there provided is a method of treating a femur and a tibia of a knee, the method comprising: preparing a distal surface of the femur; attaching a femoral trial component in accordance with the first aspect of the invention to the distal surface of the femur; positioning a tibial cutting jig in proximity to the tibia; coupling the tibial cutting jig to the femoral trial component via a first fastening point; reversibly securing the tibial cutting jig to the tibia; uncoupling the tibial cutting jig from the femoral trial component; and using the tibial cutting jig to resurface the tibia.

If the femoral trial component is provided with a second fastening point as mentioned above, for example at an angle of substantially 90 degrees from the first fastening point, then the above step of coupling the tibial cutting jig to the femoral trial component via the first fastening point may be performed with the femur and tibia in a first position relative to one another, and the method may further comprise, after coupling the tibial cutting jig to the femoral trial component via the first fastening point, and before reversibly securing the tibial cutting jig to the tibia: provisionally attaching (e.g. pinning) the tibial cutting jig to the tibia; uncoupling the tibial cutting jig from the femoral trial component; moving the femur and tibia into a second position relative to one another, through an angle corresponding to that between the first and second fastening points (of substantially 90 degrees, for example); and coupling the tibial cutting jig to the femoral trial component via the second fastening point.

When involving, in such a manner, two relative positions of the femur and tibia (i.e. two angles of flexion of the knee), preferably, in the first position, the femur and tibia are in full extension, and in the second position, the femur and tibia are at an angle of substantially 90 degrees to one another.

If only a single fastening point is provided on the femoral trial component, the fastening point may be positioned such as to couple to the tibial cutting jig at an angle of substantially 90 degrees of flexion of the knee. Such an angle is suitable for performing partial knee replacement.

Preferably the step of reversibly securing the tibial cutting jig to the tibia is performed with reference to tensioning the ligaments in the knee.

According to a third aspect of the invention there is provided a jig for use in performing femoral resurfacing, adapted to be set into a plurality of cutting angles in a range from 3° to 15°. Such a jig is highly advantageous over standard jigs (which typically provide cutting angles limited to a range of 3° to 7°), since those standard jigs do not provide sufficient angular adjustment for use with our ligament reference knee replacement technique as described herein, in which we typically cut at an angle of around 8-10°.

As those skilled in the art will appreciate, the present apparatus and method are not only applicable to the treatment of a knee, but can be adapted for use in any joint resurfacing procedure where one articular surface is intricately linked by ligament tensions to a reciprocal surface (e.g. ankle, elbow, small joints of hand/foot, etc.).

Thus, more generally, according to a fourth aspect of the invention there is provided a trial component for attachment to a prepared surface of a first bone (for example, but not limited to, a femur), the trial component comprising a fastening point for coupling (in a substantially rigid yet temporary manner) the trial component to a cutting jig for cutting the surface of a second bone (for example, but not limited to, a tibia) opposing the first bone.

The said fastening point may be a first fastening point, and the trial component may further comprise a second fastening point for coupling the trial component to the cutting jig, the first and second fastening points being at a predetermined angle (for example, but not limited to, substantially 90 degrees) to one another. One or more additional fastening points, at other predetermined angles, may also be provided on the trial component, in addition to the first and second fastening points.

The trial component may have a cut-out region for accommodating one or more ligaments.

The trial component may be provided in a set of parts together with a said cutting jig, and coupling means for reversibly coupling the cutting jig to the trial component via the first fastening point.

If the trial component is provided with a second fastening point, or additional fastening point(s), then the coupling means provided in the set of parts are for reversibly coupling the cutting jig to the trial component via the first fastening point and, separately, via the second (or additional) fastening point(s).

According to a fifth aspect of the invention there is provided a method of treating a first bone (for example, but not limited to, a femur) and an opposing second bone (for example, but not limited to, a tibia) of a joint (for example, but not limited to, a knee), the method comprising: preparing a surface of the first bone; attaching a trial component to the prepared surface of the first bone; positioning a cutting jig in proximity to the second bone; coupling the cutting jig to the trial component via a first fastening point; reversibly securing the cutting jig to the second bone; uncoupling the cutting jig from the trial component; and using the cutting jig to resurface the second bone.

If the trial component is provided with a second fastening point as mentioned above, at a predetermined angle from the first fastening point, then the above step of coupling the cutting jig to the trial component via the first fastening point may be performed with the first bone and the second bone in a first position relative to one another, and the method may further comprise, after coupling the cutting jig to the trial component via the first fastening point, and before reversibly securing the cutting jig to the second bone: provisionally attaching (e.g. pinning) the cutting jig to the second bone; uncoupling the cutting jig from the trial component; moving the first bone and second bone into a second position relative to one another, through the said predetermined angle (e.g. substantially 90 degrees); and coupling the cutting jig to the trial component via the second fastening point.

Preferably the step of reversibly securing the cutting jig to the second bone is performed with reference to tensioning the ligaments in the joint.

BRIEF DESCRIPTION OF THE DRAWINGS

Embodiments of the invention will now be described, by way of example only, and with reference to the drawings in which:

FIG. 3 illustrates a femoral trial component according to an embodiment of the invention, with FIG. 3a illustrating a plan view of the femoral trial component (including a cut-out region for accommodating an anterior cruciate ligament) and FIG. 3b illustrating a cross-section of the femoral trial component (showing first and second fastening points, at 90 degrees to one another, for coupling the femoral trial component to a tibial cutting jig);

In the figures, like elements are indicated by like reference numerals throughout.

DETAILED DESCRIPTION OF PREFERRED EMBODIMENTS

The present apparatus and method creates an anatomic femoral resurfacing with a corresponding tibial resurfacing sympathetic to the soft tissue envelope, with an aim to restore normal joint line height, joint line obliquity and tibial slope. This will allow the soft tissue envelope to behave as near to normal as can be achieved given the geometry and material constraints of conventional (e.g. TKA) prosthesis designs. An ideal prosthesis is considered to have a single or near-single radius of curvature, or potentially a smaller radius of curvature of the lateral femoral condyle in the higher flexion range, dished medial poly, flatter lateral poly to allow for increased roll back in deeper flexion, and a cut-out to allow for anterior cruciate ligament (ACL) preservation.

In one embodiment the present surgical technique may therefore be considered to be a "femur first ligament respecting total knee arthroplasty".

Surgical Technique

The surgical technique developed in the present work uses standard surgical exposure of the knee joint, being mindful of normal ligament structures, and is as follows:

A. Anatomical Femoral Resurfacing

Aim for symmetrical distal and posterior cuts of both medial and lateral sides of the thickness of the femoral component, typically 9-10 mm. This is in contrast to conventional mechanically aligned technique and will place the femoral component in a more anatomical position.

Surgical options:

1. Pre operation determination of valgus cut using radiographic assessment to determine the Distal Femoral Articular Angle (DFAA) and posterior cuts using measured resection with 0 degrees of external rotation (ER) from posterior condylar axis.
2. Reference from intramedullary (IM) femoral alignment rod (ideally flexible to allow for some flexion of femoral component) with paddles fitted to distal jig to allow for varying amounts of cartilage wear. If full thickness (FT) cartilage loss from medial femoral condyle a 2-3 mm pad is fitted under the distal femoral block medially (if there is not FT loss medially then remaining cartilage could be curetted to allow pad to reference from sub-chondral bone plate). The expected distal femoral cut angle would normally be expected to be in a range from 6 degrees to 11 degrees of valgus.

Figure 1:
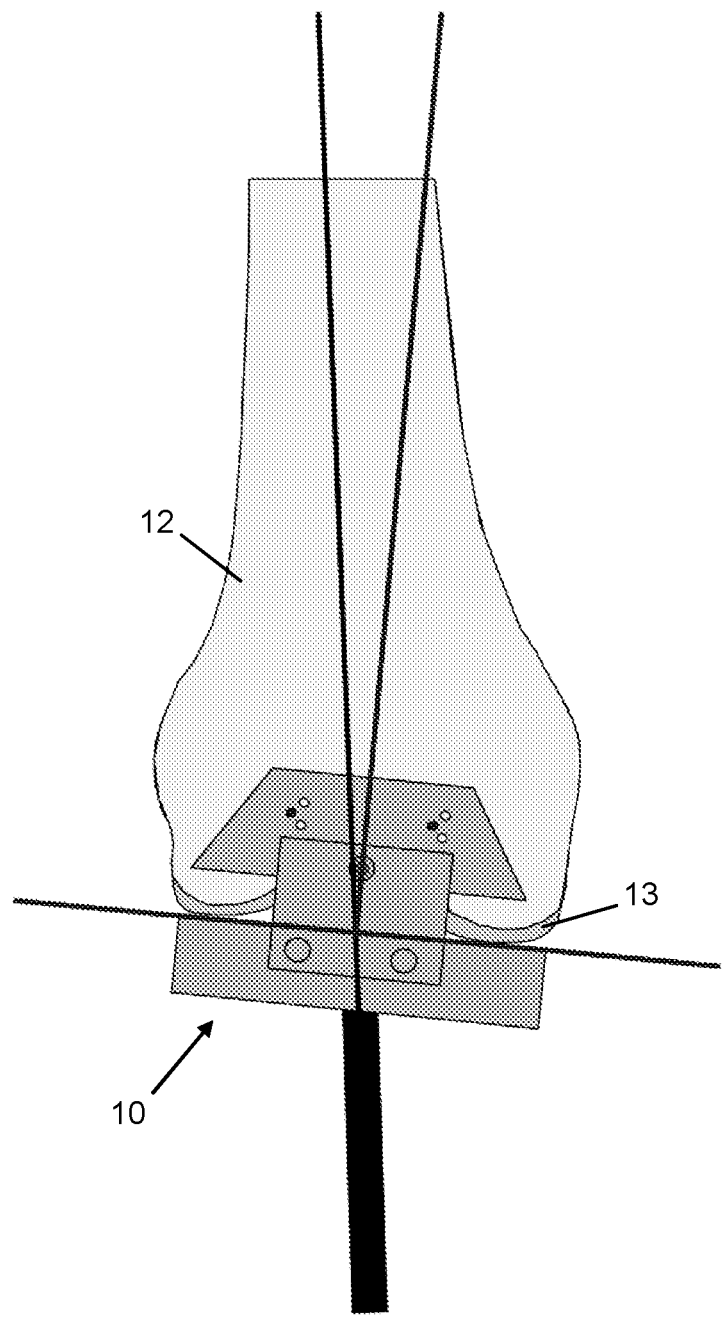
FIG. 1 illustrates a jig for use in performing femoral resurfacing, for making a distal femoral cut (similar to a standard jig for this purpose, but reengineered by us so as to provide cutting angles in a range from 3° to 15°, for use with our present ligament reference knee replacement technique)

FIG. 1 shows one possible jig 10 for use in performing such resurfacing of a distal articulating surface 13 of a femur 12. The jig 10 is similar to a standard jig for this purpose, but reengineered by us so as to provide cutting angles in the range from 3° to 15°, for use with our present ligament reference knee replacement technique. Using this jig 10, we typically cut at an angle of around 8-10°.

Figure 2:
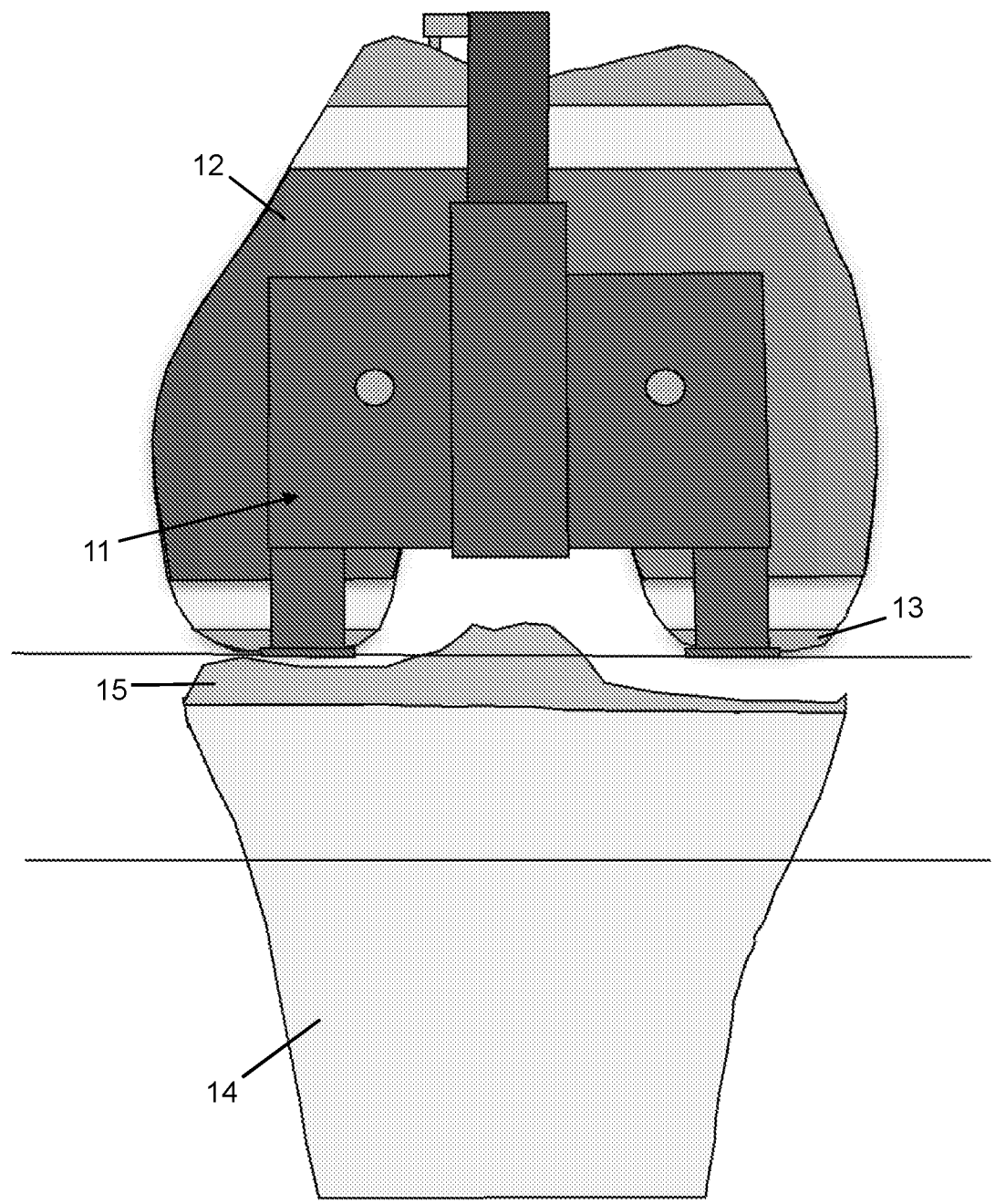
FIG. 2 illustrates an alternative pre-existing jig for use in performing femoral resurfacing, for assessing femoral rotation.

The posterior cut would be made using a measured resection technique (if no posterior cartilage loss then a 0 degree ER guide could be used making symetrical medial and lateral posterior condyle resections. FIG. 2 shows an alternative (pre-existing) jig 11 for use in setting neutral rotation for making femoral bony cuts, for performing such resurfacing of a distal articulating surface 13 of a femur 12. An opposing tibia 14 (with articular cartilage 15) is also illustrated.

If there is cartilage wear then a pad could be fitted to allow for an estimation of the amount of cartilage loss.
3. Using a patient-specific instrumentation (PSI) guide aiming for anatomic femoral resurfacing (using sub-chondral bone as reference with estimation of normal cartilage thickness).

B. Femoral Trialing

Using a post referencing technique the femur is sized and appropriate anterior and chamfer cuts are made (taking care to avoid damage to ACL if this is intact and is to be retained).

The appropriate femoral component can be trialled.

FIG. 3 illustrates a femoral trial component 16 according to an embodiment of the invention, which may be made, for example, from surgical grade stainless steel. FIG. 3a illustrates a plan view of the femoral trial component 16, including a cut-out region 17 for accommodating and preserving an anterior cruciate ligament, and fastening holes 18 and 19 for attaching the femoral trial component 16 to the femur 12. FIG. 3b illustrates a cross-section of the femoral trial component 16, showing a first fastening point 20 and a second fastening point 21 for coupling the femoral trial component 16 to a tibial cutting jig (25, as discussed below). The first fastening point 20 and the second fastening point 21 are at 90 degrees to one another. The femoral trial component 16 includes chamfered internal surfaces 22 and 23 to complement corresponding chamfering made to the distal surface 13 of the femur 12.

The knee is brought slowly into full extension to check adequate distal femur has been resected (a small fixed flexion deformity (FFD) may be accepted at this stage if there are significant posterior osteophytes).

The patella tracking is noted and as the knee is bought into terminal extension an estimate of optimal tibial component rotation can be gauged with a mark made anteriorly on the tibial plateau corresponding to the anterior aspect of the intercondylar notch.

C. Assessment of Soft Tissue Envelope

Excess osteopytes should be removed.

With the knee in extension the (varus) deformity can be manually corrected and then a rough estimate of the overall leg alignment can be made.

Figure 4:
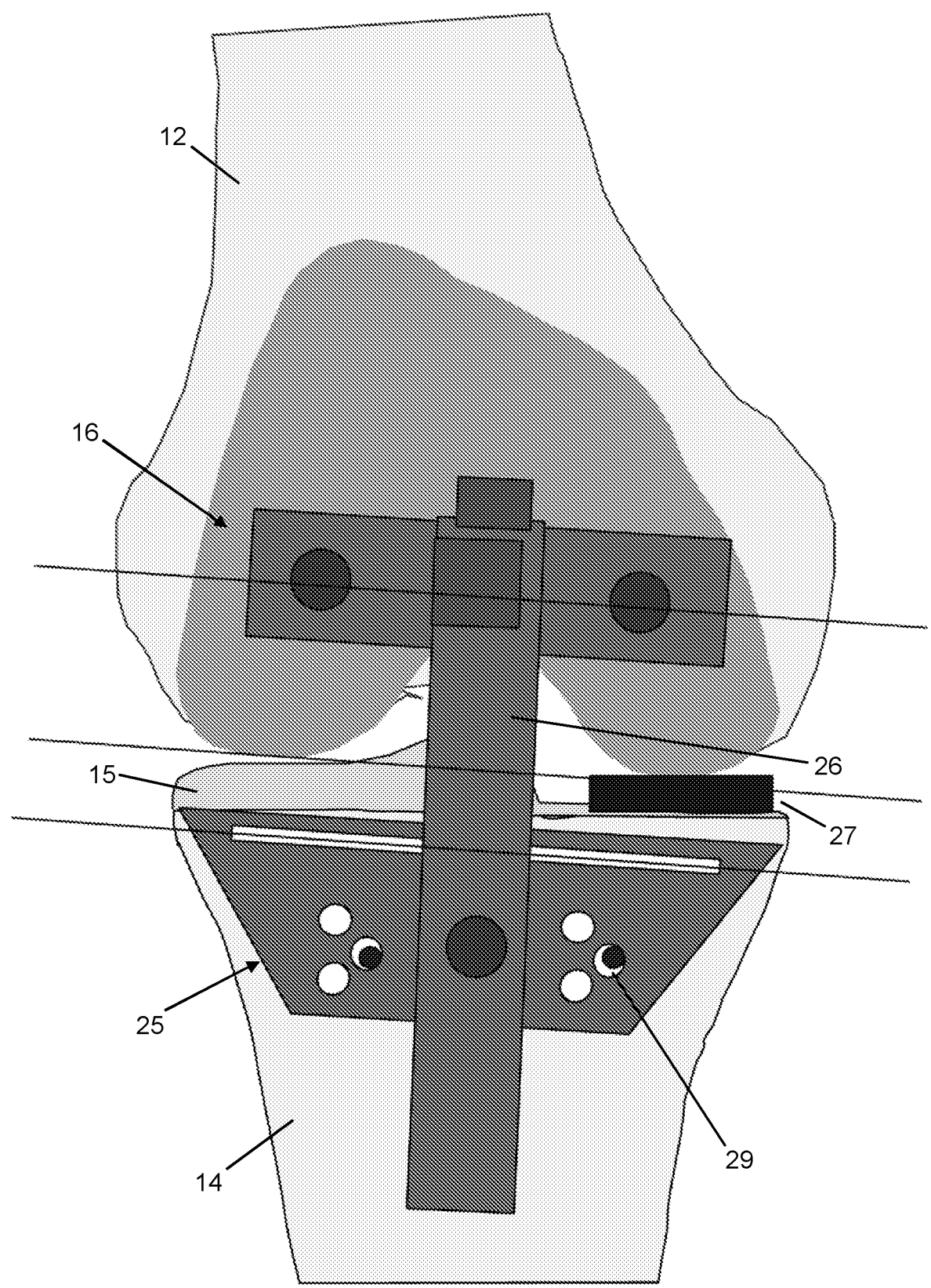
FIG. 4 illustrates the femoral trial component of FIG. 3 attached to a femur, and coupled (in a substantially rigid yet temporary manner) to a tibial cutting (or "resection") jig which has subsequently been attached to the tibia, with the knee in extension, and with a spacer/tensioning device having been inserted between the femur and the tibia to allow restoration of normal soft tissue tensions.

As shown in FIG. 4, spacers (or tensioners) 27 of various thickness can be inserted into the medial compartment to allow for correction of the medial collateral ligament (MCL) out to an appropriate physiological tension. FIG. 4 shows the femoral trial component 16 (as in FIG. 3) viewed from the front, linked to a tibial cutting jig 25. The tibial cutting jig 25 may be made, for example, from surgical grade stainless steel.

Figure 8:
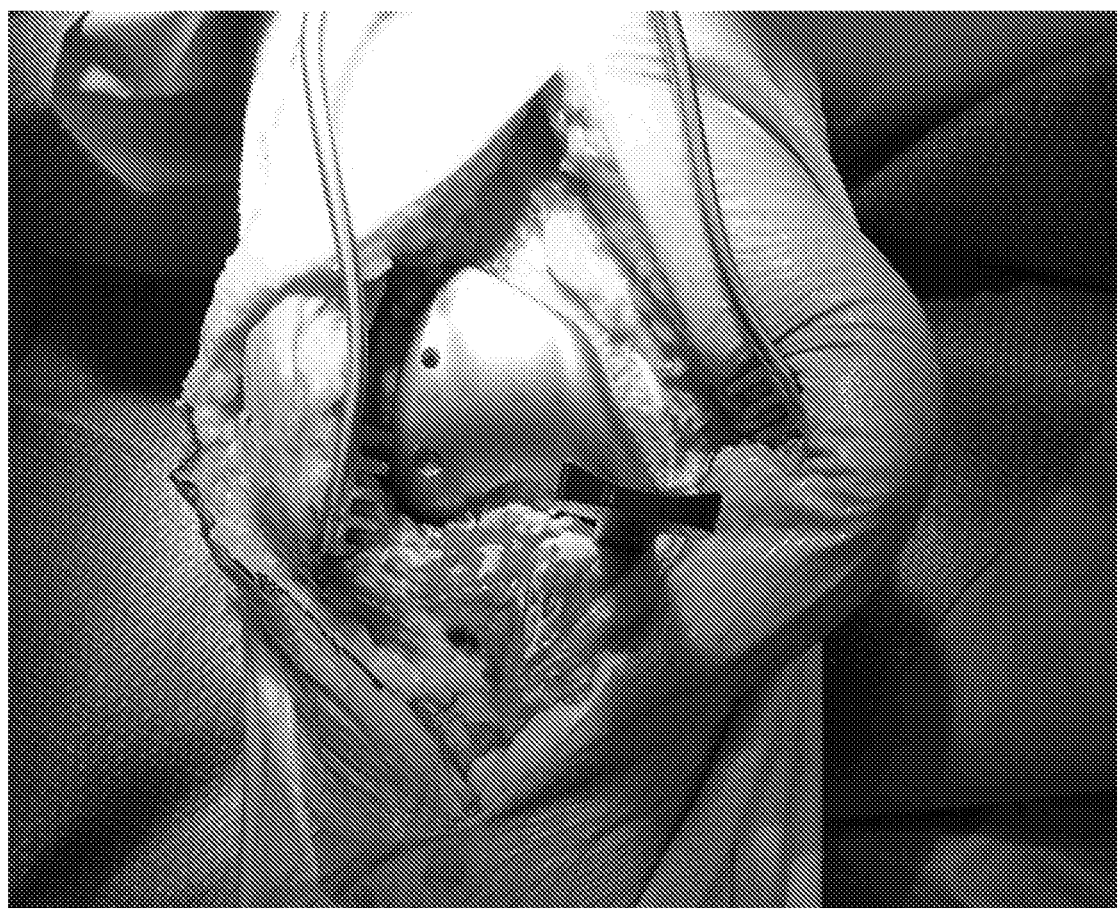
FIG. 8 is a photograph (mock-up) of part of a knee arthroplasty procedure.

A photograph of a mock-up of this stage in the procedure is provided as FIG. 8.

Figure 5:
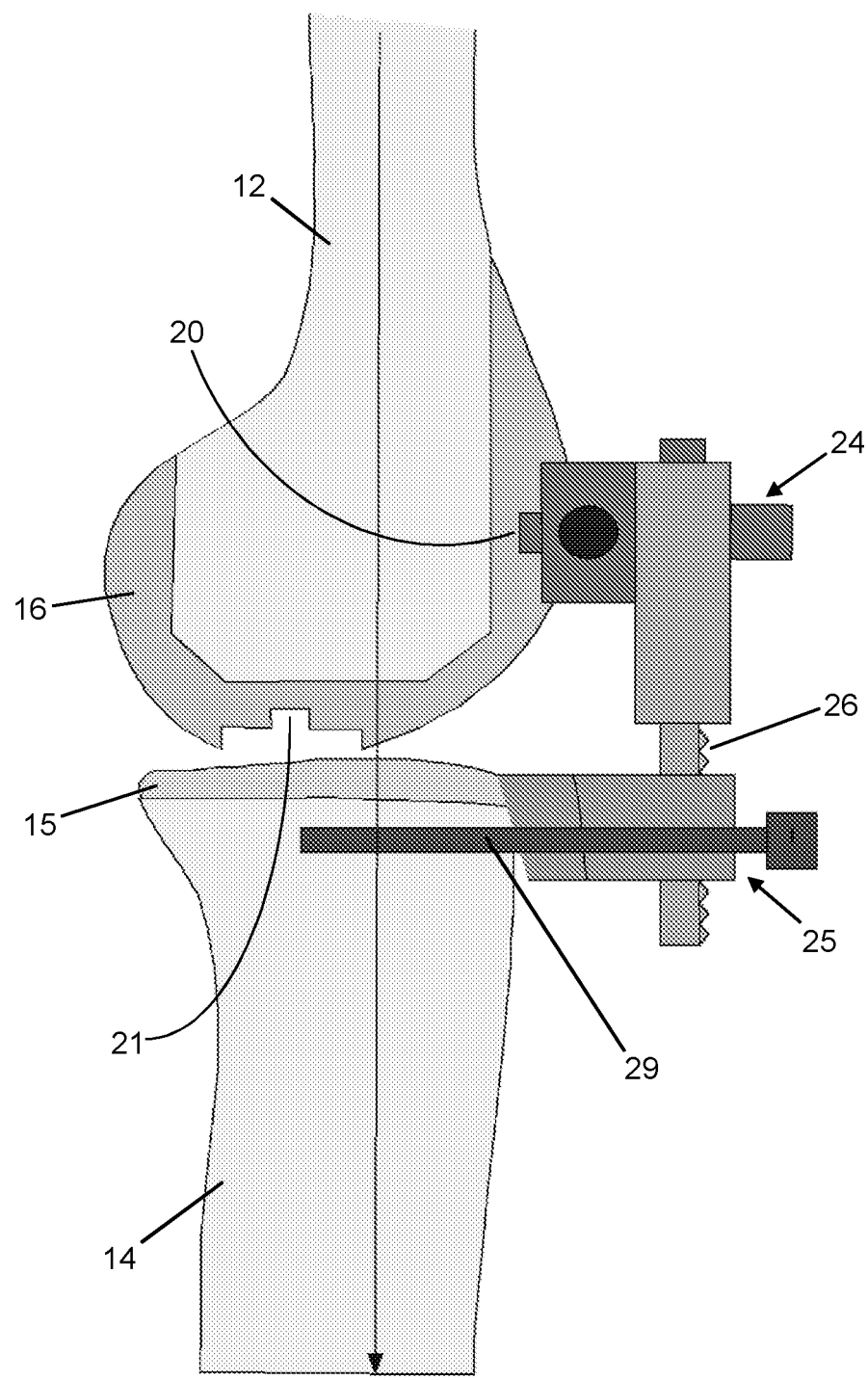
FIG. 5 illustrates the femoral trial component and tibial cutting jig of FIG. 4 (viewed through an angle of 90 degrees relative to FIG. 4), the tibial cutting jig being coupled to the femoral trial component with the knee in extension.

In more detail, and with reference to FIG. 5 (which corresponds to the arrangement shown in FIG. 4 but viewed through an angle of 90 degrees relative to FIG. 4), with the knee in extension a tibial cutting jig 25 can be positioned. This is linked to the femoral trial component 16, ensuring that the tibial resection will be parallel to the distal femoral articulating surface (thereby restoring the normal joint line height and obliquity in extension). The depth of resection can be assessed in extension from cutting an appropriate amount referenced from the distal surface of the femoral trial.

As illustrated, the femoral trial component 16 is coupled to the tibial cutting jig 25 via a fastening member 24 that is attached to the first fastening point 20 of the femoral trial component 16. The fastening member 24 is then coupled to the tibial cutting jig 25 via an adjustable coupling member 26 (the tibial cutting jig 25 having a fastening point to which the coupling member 26 attaches). The fastening member 24 and the coupling member 26 may be made, for example, from surgical grade stainless steel and provide substantially rigid (yet temporary and reversible) coupling between the femoral trial component 16 and the tibial cutting jig 25.

The tibial cutting jig 25 is provisionally pinned using pins 29. The alignment of the tibial resection will normally range from neutral to a 5 degree varus cut.

D. Tibial Resection

The tibial jig 25 is then uncoupled from the femoral trial component 16, by detaching the coupling member 26 from the tibial cutting jig 25, and by detaching the fastening member 24 from the first fastening point 20 of the femoral trial component 16.

Figure 6:
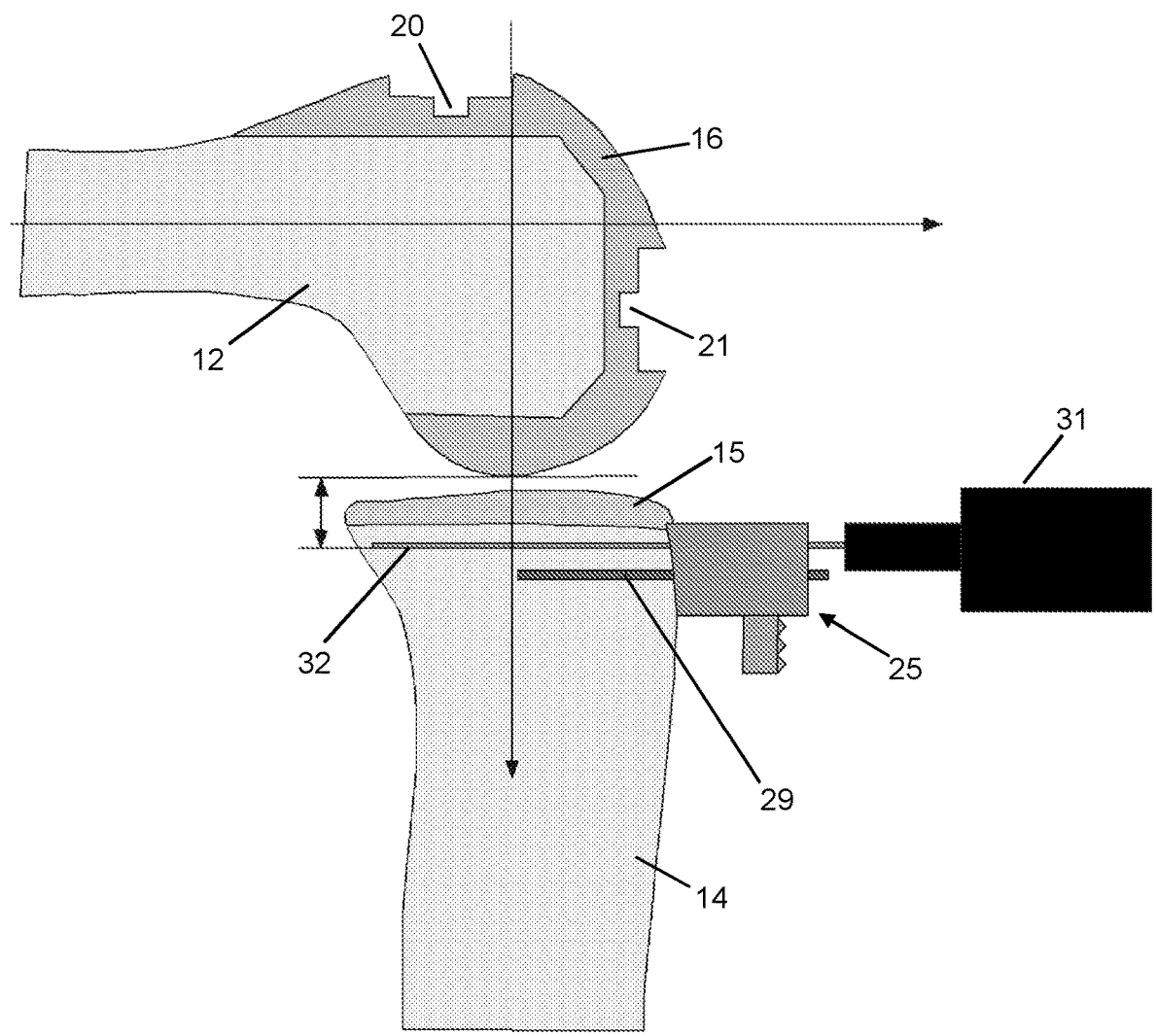
FIG. 6 illustrates the femoral trial component of FIG. 5 uncoupled from the tibial cutting jig and with the knee having been brought into 90 degrees of flexion.

The spacer 27 is removed from the medial compartment and the knee is bought into 90 degrees of flexion, as illustrated in FIG. 6. An appropriate spacer block is selected and reinserted into the medial compartment (posterior portion) to allow for physiological tensioning of the medial compartment.

The plane of the tibial cut is reassessed. It should be parallel to the posterior condyles of the trial.

Figure 7:
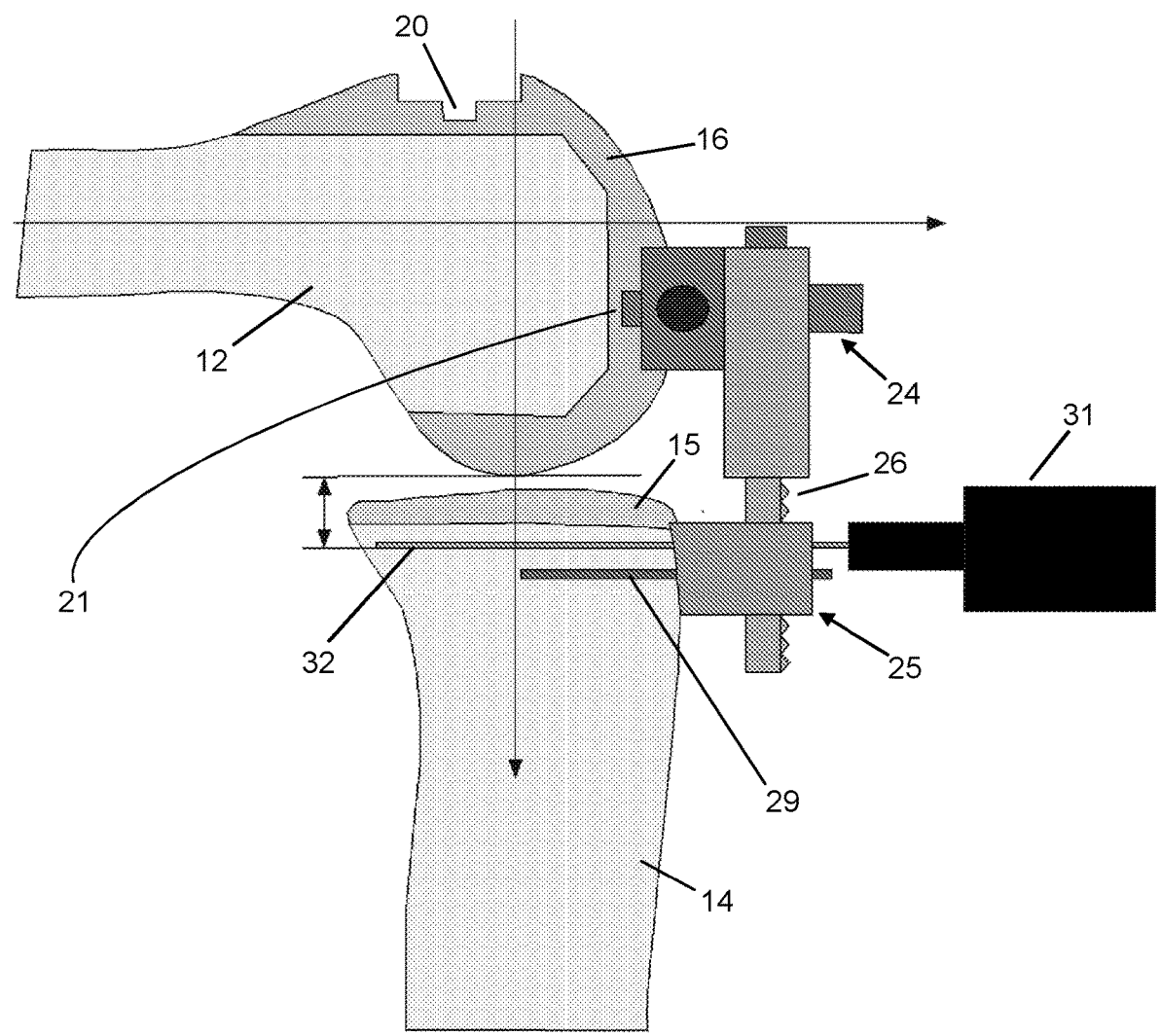
FIG. 7 illustrates the femoral trial component of FIG. 5 recoupled to the tibial cutting jig, with the knee in 90 degrees of flexion, in order to confirm that adequate resection of the tibia is taking place in both extension and flexion.

As illustrated in FIG. 7, the tibial cutting jig 25 can then be reconnected to the femoral trial component 16 to confirm appropriate orientation and depth of resection. This is performed by attaching the fastening member 24 to the second fastening point 21 of the femoral trial component 16, and by coupling the fastening member 24 to the tibial cutting jig 25 using the coupling member 26.

Figure 9:
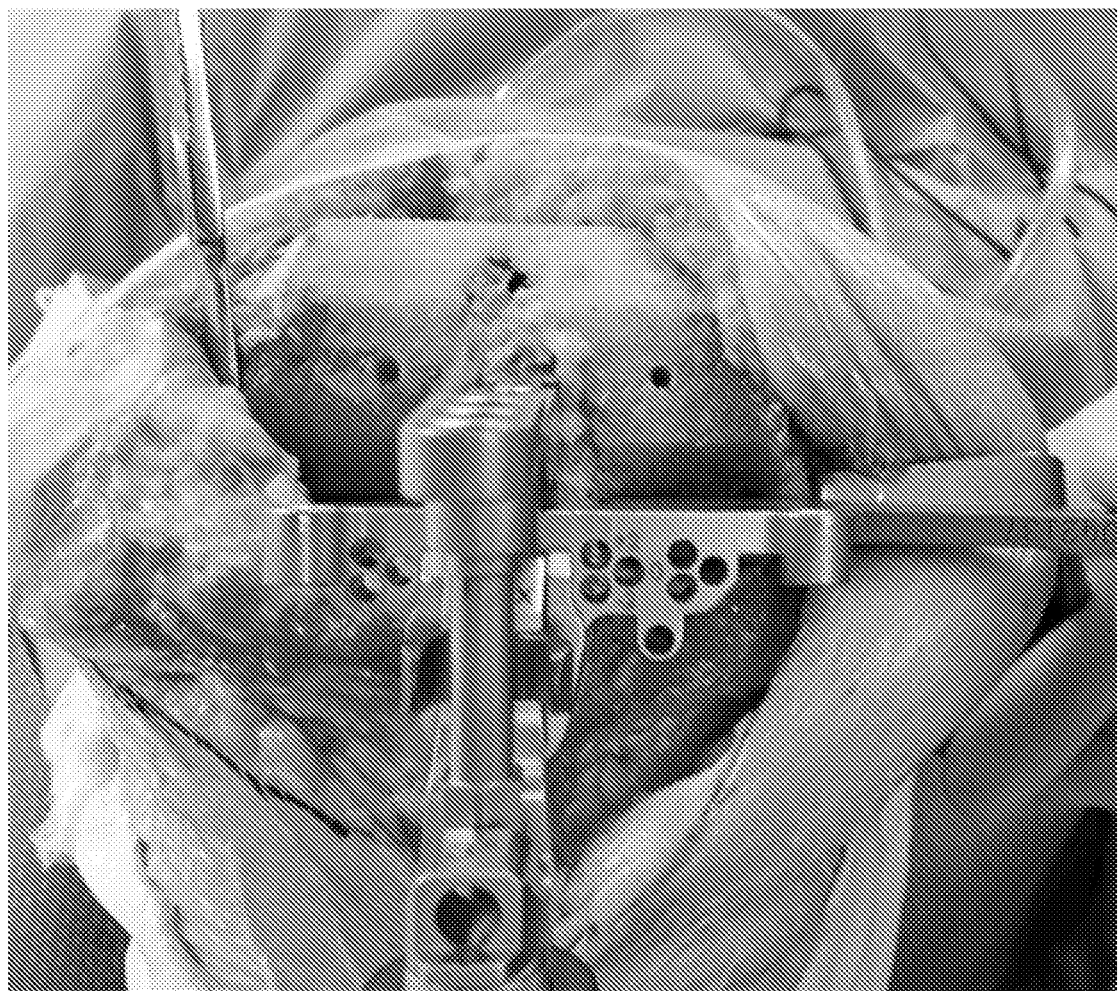
FIG. 9 is a photograph (mock-up) of a subsequent part of a knee arthroplasty procedure.

A photograph of a mock-up of this stage in the procedure is provided as FIG. 9.

The depth of resection is measured with reference to the posterior condyles. If this equates to the resection space in extension then the tibial cutting jig 25 can be secured. If the flexion gap measures less than the anticipated extension gap then more slope can be dialed into the tibial cutting jig 25 to allow for a deeper resection posteriorly.

In either flexion or extension the final orientation and resection level of the tibial cutting jig 25 is determined by tensioning the ligaments to their physiological length using a spacer/tensioner.

When the position of the tibial cutting jig 25 is confirmed it can be secured (reversibly) to the tibia 14 by the use of drill pins. The tibial cutting jig 25 can then be uncoupled from the femoral trial component 16, and the coupling device 26 removed.

A tibial cut can be then made (medial and lateral tibial biscuit cuts made for ACL preservation) using a saw 31 (having a saw blade 32) guided by the tibial cutting jig 25. The plane of this cut should be parallel to the femoral trial component 16 throughout the functional range of motion while respecting the physiological tensions within the soft tissue envelope of the knee.

Figure 10:
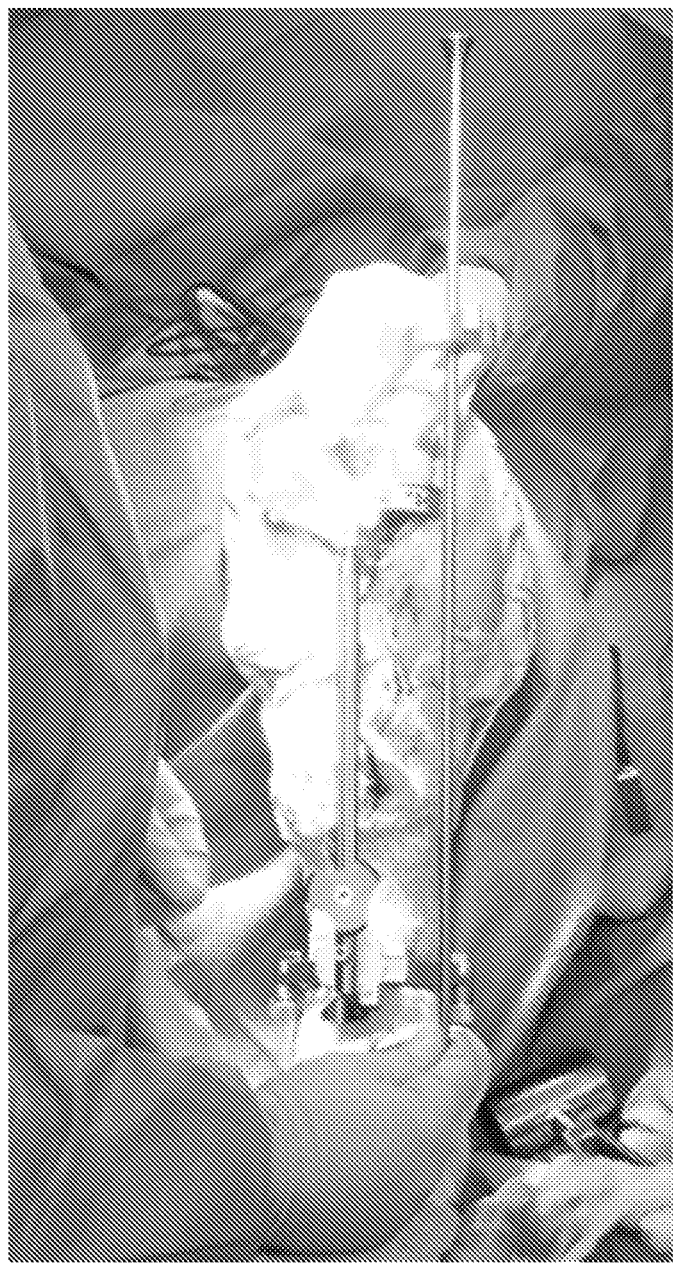
FIG. 10 is a photograph (mock-up) of a subsequent part of a knee arthroplasty procedure.

A photograph of a mock-up of this stage in the procedure is provided as FIG. 10.

E. Final Preparation of Tibia

A trial plate is positioned with trial bearing(s) of appropriate thickness. The knee is taken through a range of motion to assess tensions in collateral ligaments throughout the range (in flexion of >45 degrees the lateral compartment will have some laxity and with the knee in a "FIG. 4" position there will be opening in the lateral compartment).

Adequate patella tracking should be confirmed.

Rotation of the tibial component can be assessed and confirmed with the previous marking on the anterior tibial plateau.

Keel slots and/or lug holes can be made for the definitive components.

F. Component Implantation

Patella resurfacing can be made in a standard fashion if indicated.

Knee surfaces are thoroughly washed and drill holes made in sclerotic bone to allow for optimal cement penetration Definitive components are implanted as per standard technique.

Figure 11:
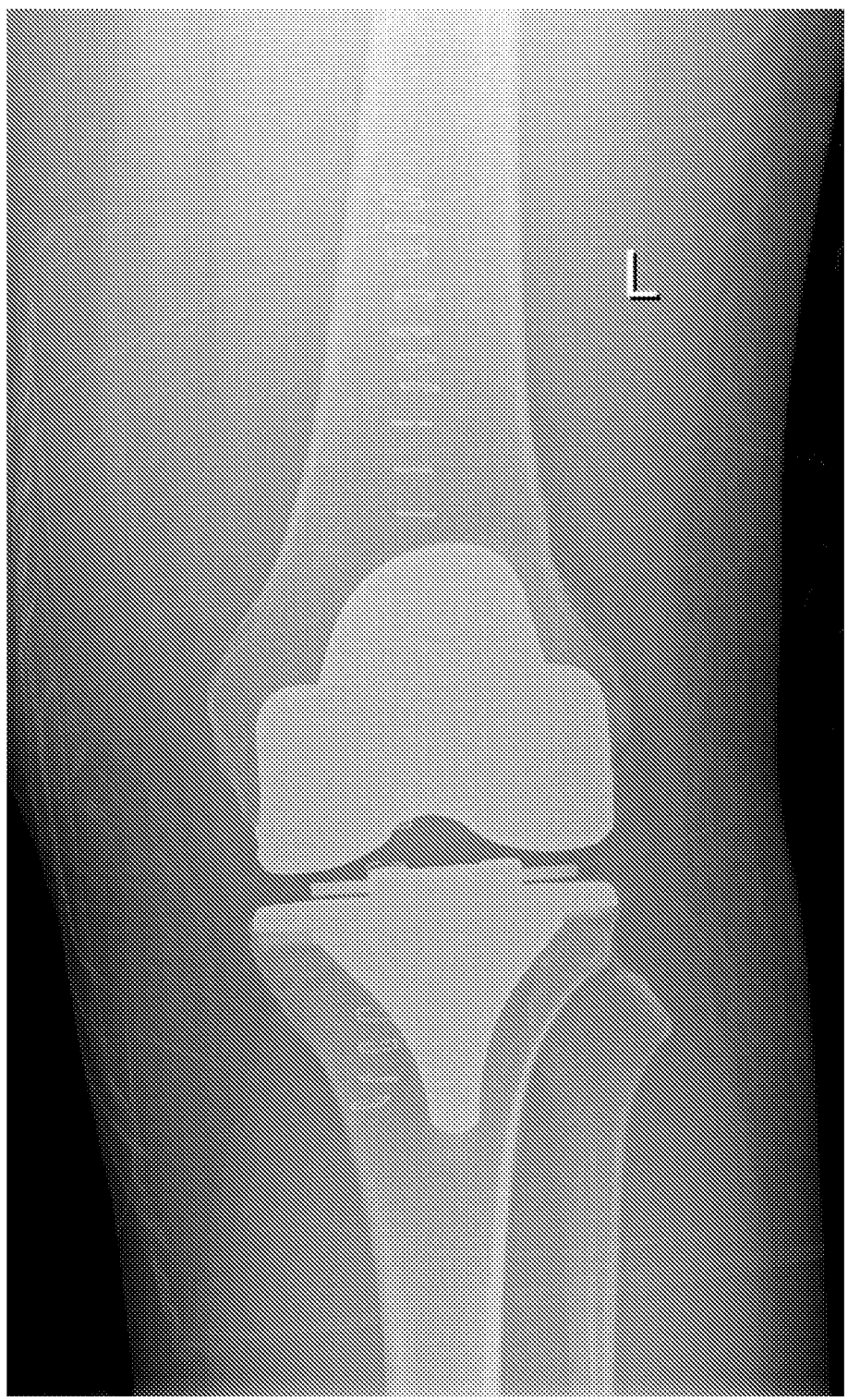
FIG. 11 is an X-ray photograph of a completed a knee arthroplasty procedure.

FIG. 11 shows an X-ray photograph of a completed a knee arthroplasty procedure.

Modifications, Alternative Embodiments and Other Variants

Although, in the above embodiments, two fastening points (20 and 21) are provided on the femoral trial component 16, at a predetermined angle of 90 degrees to one another, in other embodiments one or more additional fastening points, at other predetermined angles, may also be provided on the femoral trial component 16, in addition to fastening points 20 and 21.

Figure 12:
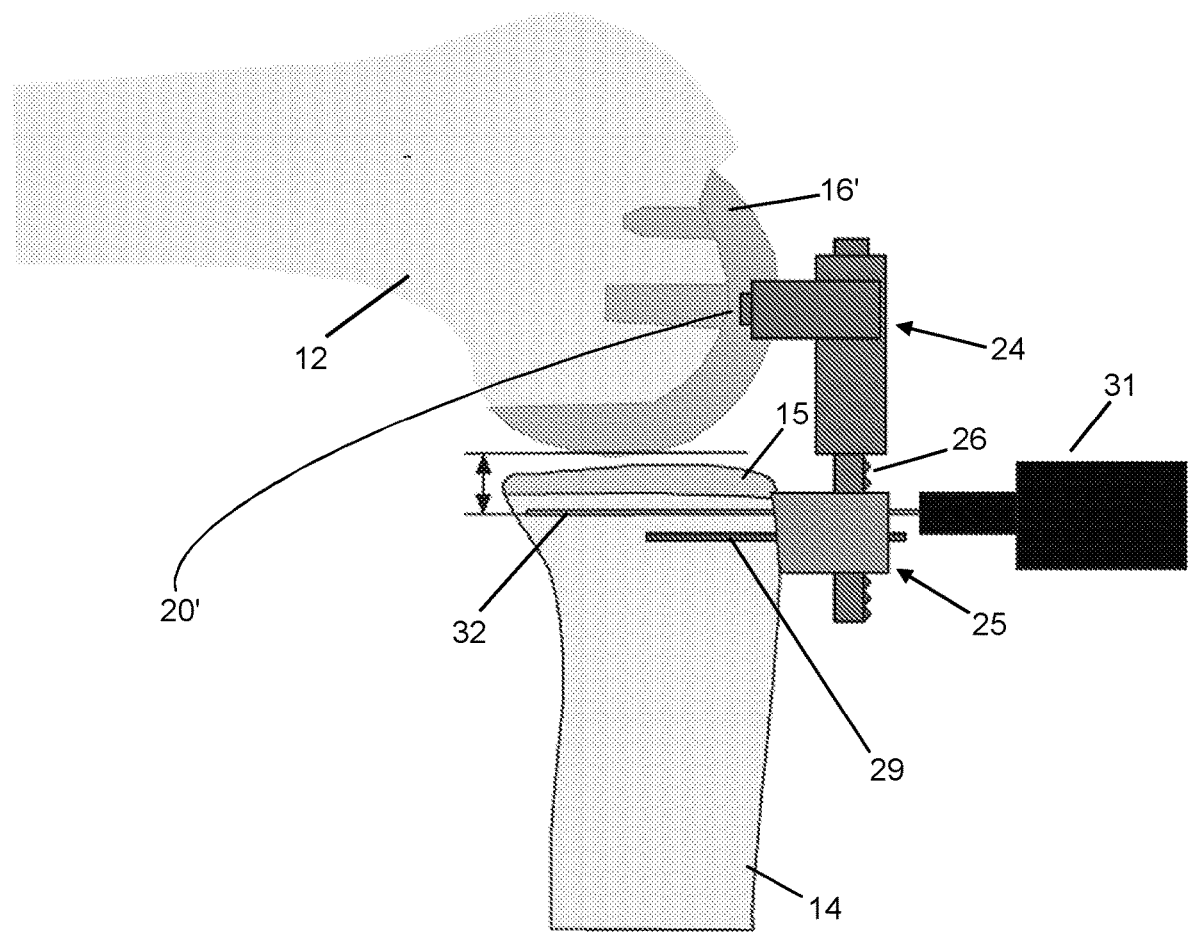
FIG. 12 is an illustration of a partial knee replacement femoral trial component with a fastening point to allow coupling to a tibial cutting (or "resection") jig that allows appropriate resection of tibial bone after physiological tensioning of the ligaments, with a spacer/tensioner.

With reference now to FIG. 12, for performing partial knee replacement a modified femoral trial component 16' can be used, having only a single fastening point 20'. The modified femoral trial component 16' is coupled to a tibial cutting jig 25 via the single fastening point 20', with the knee in flexion or extension after appropriate ligament tensioning. In this way a predictable and appropriate amount of bone is resected with reference to an anatomically placed femoral trial component and physiological tension in the ligaments (a femur first, ligament referenced technique for partial knee replacement).

Although described above in relation to treating a femur and a tibia of a knee, the present technique can in principle be applied to any joint resurfacing procedure where one articular surface is intricately linked by ligament tensions to a reciprocal surface (e.g. ankle, elbow, small joints of hand/foot, etc.).

Thus, more generally, the present work provides a trial component (e.g. 16) for attachment to a prepared surface of a first bone (for example, but not limited to, a femur 12), the trial component comprising a fastening point (e.g. 20) for coupling the trial component to a cutting jig (e.g. 25) for cutting the surface of a second bone (for example, but not limited to, a tibia 14) opposing the first bone.

The said fastening point (e.g. 20) may be a first fastening point, and the trial component may further comprise a second fastening point (e.g. 21) for coupling the trial component to the cutting jig, the first and second fastening points being at a predetermined angle (for example, but not limited to, 90 degrees) to one another. One or more additional fastening points, at other predetermined angles, may also be provided on the trial component, in addition to the first and second fastening points.

The trial component may have a cut-out region for accommodating one or more ligaments.

The trial component may be provided in a set of parts together with a said cutting jig, and coupling means for reversibly coupling the cutting jig to the trial component via the first fastening point.

If the trial component is provided with a second fastening point, or additional fastening point(s), then the coupling means provided in the set of parts are for reversibly coupling the cutting jig to the trial component via the first fastening point and, separately, via the second (or additional) fastening point(s).

In general terms, a corresponding method is provided, for treating a first bone (for example, but not limited to, a femur 12) and an opposing second bone (for example, but not limited to, a tibia 14) of a joint (for example, but not limited to, a knee), the method comprising: preparing a surface of the first bone; attaching a trial component (e.g. 16) to the prepared surface of the first bone; positioning a cutting jig (e.g. 25) in proximity to the second bone; coupling the cutting jig to the trial component via a first fastening point; reversibly securing the cutting jig to the second bone; uncoupling the cutting jig from the trial component; and using the cutting jig to resurface the second bone.

If the trial component is provided with a second fastening point as mentioned above, at a predetermined angle from the first fastening point, then the above step of coupling the cutting jig to the trial component via the first fastening point may be performed with the first bone and the second bone in a first position relative to one another, and the method may further comprise, after coupling the cutting jig to the trial component via the first fastening point, and before reversibly securing the cutting jig to the second bone: provisionally attaching (e.g. pinning) the cutting jig to the second bone; uncoupling the cutting jig from the trial component; moving the first bone and second bone into a second position relative to one another, through the said predetermined angle (e.g. 90 degrees); and coupling the cutting jig to the trial component via the second fastening point.

Preferably the step of reversibly securing the cutting jig to the second bone is performed with reference to tensioning the ligaments in the joint.

The invention claimed is:

1. A kit comprising:
 a femoral trial component for attachment to a prepared distal surface of a femur, the femoral trial component comprising at least two fastening points including a first fastening point configured for coupling the femoral trial component to a tibial cutting jig at a first angle and a second fastening point configured for coupling the femoral trial component to the tibial cutting jig at a second angle, wherein, the second angle is different from the first angle;
 a tibial cutting jig; and
 coupling means for reversibly coupling the tibial cutting jig to the femoral trial component, wherein the coupling means are for reversibly coupling the tibial cutting jig to the femoral trial component via the first fastening point and, separately, via the second fastening point.

2. The kit as claimed in claim 1, wherein wherein at the first angle the femur and tibia are in full extension, and wherein at the second angle the femur and tibia are at flexion an angle of substantially 90 degrees to one another.

3. The kit as claimed in claim 1, having a cut-out region for accommodating an anterior cruciate ligament.

4. The kit of claim 1, wherein the first fastening point is configured for coupling a femur when attached to the femoral trial component to a tibia when attached to the tibial cutting jig in extension and the second fastening point configured for coupling a femur to a tibia in flexion.

5. The kit of claim 4, wherein the first fastening point is configured to couple a femur and a tibia in full extension and the second fastening point is configured to couple a femur and a tibia at flexion at an angle of substantially 90 degrees to full extension.

6. A method of treating a femur and a tibia of a knee, the method comprising:
 providing a femoral trial component for attachment to a prepared distal surface of a femur, the trial component comprising a first and a second fastening point for coupling the femoral trial component to a tibial cutting jig;
 preparing a distal surface of the femur;
 attaching the femoral trial component to the prepared distal surface of the femur;
 positioning a tibial cutting jig in proximity to the tibia;
 coupling the tibial cutting jig to the femoral trial component via the first fastening point;
 reversibly securing the tibial cutting jig to the tibia;
 uncoupling the tibial cutting jig from the femoral trial component; and
 using the tibial cutting jig to resurface the tibia, wherein the step of coupling the tibial cutting jig to the femoral trial component via the first fastening point is performed with the femur and tibia in a first position relative to one another,
 and the method further comprising, after coupling the tibial cutting jig to the femoral trial component via the first fastening point, and before reversibly securing the tibial cutting jig to the tibia:
 provisionally attaching the tibial cutting jig to the tibia;
 uncoupling the tibial cutting jig from the femoral trial component;
 moving the femur and tibia into a second position relative to one another, through an angle corresponding to that between the first and the second fastening points; and
 coupling the tibial cutting jig to the femoral trial component via the second fastening point.

7. The method as claimed in claim 6, wherein in the first position, the femur and tibia are in full extension, and wherein, in the second position, the femur and tibia are at flexion an angle of substantially 90 degrees to one another.

8. The method as claimed in claim 6, wherein the step of reversibly securing the tibial cutting jig to the tibia is performed with reference to tensioning the ligaments in the knee.

9. A trial component for attachment to a prepared surface of a first bone, the trial component comprising:
 at least two fastening points including a first fastening point configured for coupling the trial component at a first angle to a cutting jig for cutting the surface of a second bone opposing the first bone and a second fastening point configured for coupling the trial component to the cutting jig at a second angle, the second angle being different than the first angle;
 together with a cutting jig; and
 coupling means for reversibly coupling the cutting jig to the trial component, wherein the coupling means are for reversibly coupling the cutting jig to the trial component via the first fastening point and, separately, via the second fastening point.

10. The trial component as claimed in claim 9, wherein wherein at the first angle the first bone and second bone are in full extension, and wherein at the second angle the first bone and second bone are at flexion an angle of substantially 90 degrees to one another.

11. The trial component as claimed in claim 9, having a cut-out region for accommodating one or more ligaments.

12. The trial component of claim 9, wherein the first fastening point is configured for coupling the first bone when attached to the trial component to the second bone when attached to the cutting jig in extension and the second fastening point configured for coupling the first bone to the second bone in flexion.

13. The trial component of claim 12, the first fastening point is configured to couple the first bone and the second bone in full extension and the second fastening point is configured to couple the first bone and the second bone at flexion at an angle of substantially 90 degrees to full extension.

14. A method of treating a first bone and an opposing second bone of a joint, the method comprising:

provoiding a trial component for attachment to a prepared distal surface of the first bone, the trial component comprising a first fastening point for coupling the trial component to a second bone cutting jig;

preparing a surface of the first bone;

attaching the trial component to the prepared surface of the first bone;

positioning a cutting jig in proximity to the second bone;

coupling the cutting jig to the trial component via the first fastening point;

reversibly securing the cutting jig to the second bone;

uncoupling the cutting jig from the trial component; and using the cutting jig to resurface the second bone, wherein the step of coupling the cutting jig to the trial component via the first fastening point is performed with the first bone and the second bone in a first position relative to one another, and the method further comprises, after coupling the cutting jig to the trial component via the first fastening point, and before reversibly securing the cutting jig to the second bone:

provisionally attaching the cutting jig to the second bone;

uncoupling the cutting jig from the trial component;

moving the first bone and second bone into a second position relative to one another, through an angle corresponding to that between the first fastening point and a second fastening point; and coupling the cutting jig to the trial component via the second fastening point.

15. The method of claim 14, wherein in the first position, the femur and tibia are in full extension, and wherein, in the second position, the femur and tibia are at flexion an angle of substantially 90 degrees to one another.

* * * * *